United States Patent [19]

Spooner

[11] Patent Number: 4,542,218

[45] Date of Patent: Sep. 17, 1985

[54] METHOD OF HALOGENATING ISOCYANURIC ACID

[75] Inventor: Thomas H. Spooner, Sulphur, La.

[73] Assignee: Olin Corporation, Cheshire, Conn.

[21] Appl. No.: 570,315

[22] Filed: Jan. 13, 1984

[51] Int. Cl.$^4$ .................................. C07D 251/26
[52] U.S. Cl. ................................................ 544/190
[58] Field of Search ........................................ 544/190

[56] References Cited

U.S. PATENT DOCUMENTS 3,835,134 9/1974 Schiessl et al. ...................... 260/248

*Primary Examiner*—John M. Ford
*Attorney, Agent, or Firm*—Donald F. Clements; James B. Haglind

[57] ABSTRACT

An improved method for reacting a gas with a liquid medium and an improved reactor therefore is described. In this method, gas is fed to the liquid medium in an agitated reactor through a plurality of sparger means which are positioned in the horizontal cross sectional area of the reactor between the reactor perimeter and the central agitator vortex. In addition, the gas spargers are located in separate segments of the cross sectional area. The improved method and reactor are particularly suitable in glass lined reactors which are employed in the preparation of halogenated isocyanurates such as trichloroisocyanuric acid by the chlorination of an aqueous solution of monosodium cyanurate and hypochlorous acid.

8 Claims, No Drawings

METHOD OF HALOGENATING ISOCYANURIC ACID

DESCRIPTION

This invention relates to a method of reacting a gaseous reactant with a liquid medium. It also includes an improved reactor design therefore.

Numerous compounds are prepared by the reaction of a gaseous reactant with a liquid medium. This occurs frequently in the preparation of halogenated compounds such as chlorinated isocyanuric acids. For example, in the preparation of chlorinated isocyanuric acid such as dichloroisocyanuric acid and trichloroisocyanuric acid, the gaseous chlorine is reacted with aqueous solution of cyanuric acid which may or may not contain other reactants such as sodium hydroxide, hypochlorous acid, monosodium cyanurate and the like. Because of the highly corrosive nature of these reactants it is necessary to employ reaction vessels that are capable of resisting corrosion.

Frequently glass lined reaction vessels are utilized for this purpose. However, the number of openings in the glass lined reaction vessel perimeter should be minimized in order to obtain a strong continuous rigid glass lining in the reaction vessel, since openings in the lining tend to form points of weakness where cracking or deterioration may occur. As a result, most of the feed lines and exit lines to reaction vessels as well as agitation means enter through the top of glass lined reaction vessels.

It is difficult to obtain adequate mixing of the gaseous medium with the aqueous reaction solution when top entering agitation means are employed. In this type of reactor, side baffles and side agitators are generally not feasible and turbulence is effected through baffles attached to the top of the reaction vessel. It is difficult to use a single sparger to feed gaseous reactants in such a vessel since the central agitator shaft is generally placed in the center of the vessel. When this agitator shaft and attached impeller provide agitation for the reaction medium, a central vortex forms which is devoid of liquid medium and which also provides an escape means for the gaseous reactant provided by the single gas sparger.

As a result, a significant amount of gaseous reactant is lost in a vertical conical plane around the central shaft of the reactor, as well as at the horizontal interface between the gas phase and the liquid medium. This gas escapes through the gas exit port at the top of the vessel and must be collected and recycled. Because this gas escapes from the liquid medium before reaction, there is a need to supply a large excess of chlorine or other gaseous reactant in order to obtain complete reaction of the components of the liquid medium. Such excess gas prolongs reaction time and adds markedly to the cost of preparing the final product.

There is a need at the present time to provide an improved method of reacting gaseous reactants with a liquid medium in order to minimize the excess gaseous reactant required to effect the reaction and also to reduce the amount of time required to complete the reaction.

It is a primary object of this invention to provide an improved method of reacting a gaseous medium with a liquid medium.

It is a further object of this invention to provide an improved reactor for reacting a gaseous medium with a liquid medium.

Another object of the invention is to provide a method of inhibiting scaling on the surfaces of glass lined reactors.

It is another object of this invention to provide an improved method for reacting a halogen gas with an aqueous reactant in order to reduce the quantity of excess halogen required to effect the reaction.

Still another object of the invention is to provide an improved method of reacting a halogen with an aqueous medium in order to reduce the reaction time required to complete the desired reaction.

A further object of this invention is to provide an improved reactor for reacting a halogen gas with an aqueous reaction medium.

These and other objects of the invention will be apparent from the following detailed description of the invention.

The foregoing objects of the invention are accomplished in an improved method for reacting a gaseous reactant with a liquid medium to form a reaction product in an agitated reaction zone having a perimeter and a horizontal cross sectional area divided into a plurality of segments which comprises contacting said gaseous reactant with said liquid medium in said reaction zone through a plurality of feed locations, each of said feed locations being positioned in a different segment and located substantially equidistant from said perimeter. The improved apparatus of this invention is a glass lined reactor having a perimeter and a horizontal cross section having a plurality of segments, said reactor being provided with a top having a central agitation means and a gas feed line means entering through said top, the improvement comprising a plurality of gaseous feed lines entering said top between said perimeter and said agitation means, each of said gas feed lines being positioned in different segments.

Although one skilled in the art will recognize that the method and apparatus of this invention is useful in general for the reaction of a gaseous reactant with a liquid medium, for purposes of clarity, the invention will be described in terms of reacting chlorine with an aqueous solution of monosodium cyanurate and hypochlorous acid to produce trichloroisocyanuric acid. However, the method and apparatus are also useful in preparing other halogenated isocyanuric acids as well as other halogenated compounds.

More in detail, in the novel method of this invention, a glass lined reaction vessel is preferably employed. Although glass is frequently employed to line steel reaction vessels to inhibit corrosion, any corrosion resistant ceramic material may be employed. The reaction vessel generally is provided with a bottom having a minimum of openings such as a single discharge port for attaching a product discharge line and the like. The side of the reaction vessel is generally cylindrical in shape of any desired capacity. The cylindrical walls are generally integral with the bottom section in order that a continuous glass lining is achieved from the top of the cylinder to the center of the bottom section where the exit port is generally located.

The upper portion of the cylindrical wall is generally supplied with a glass lined flange for securing the flanged top section which is also glass lined. Suitable gasketing means is provided between the flanges. The top section of the glass lined vessel is provided with openings for a number of features. An opening is provided for a central agitator shaft which is provided with a suitable impeller means at the lower end of the shaft within the reaction vessel and a suitable motor drive at the opposite end of the agitator shaft exterior of the reaction vessel. Other openings are provided for instrumentation means such as temperature and pressure gauges and means for feeding a gaseous reactant. One opening in the top section of the glass lined reactor is provided for feeding a liquid medium to the reactor either continuously or on a batch basis. In a preferred embodiment of this invention, the liquid reaction medium is an aqueous solution of monosodium cyanurate and hypochlorous acid. If desired, these components can be added separately but it is preferred to premix them prior to feeding to the reactor in order to minimize the number of openings in the top section of the reactor. Another feature that is applied to the top section of the reactor are the baffle means which are generally secured to the top section prior to glass coating. The baffles are generally flat plates which are positioned to minimize the formation of the central conical shaped vortex around the agitator shaft. Generally at least two baffles are employed, but more baffling means may be utilized, if desired.

In the apparatus of this invention, at least two openings are provided in the top section for feeding chlorine gas or other gaseous reactants below the surface of a liquid medium contained in the reaction vessel. The chlorine feed lines which extend through the openings in the top section of the reactor connect with sparger means or other suitable piping means which discharge the chlorine below the liquid medium level. The sparger means are typically pipes which are provided with a plurality of openings in the side thereof to form jets of gas which enter the liquid medium at a plurality of points. If desired, the sparger pipes may be free of openings in the sides and all of the chlorine gas may discharge through the bottom of the pipes into the liquid medium.

In a horizontal cross sectional area through the cylindrical walls of the reactor, the cross sectional area may be divided into a number of equal segments corresponding to the number of gas sparger lines entering the top of the reactor. The number of gas sparger lines may vary from about 2 to about 6 and preferably from 2 to 3. The gas spargers are positioned preferably equidistant between the central agitator shaft and the perimeter of the reactor walls. Each gas sparger is located in a different segment of the cross sectional area. Sufficient chlorine is fed to the liquid reaction medium to provide at least the stoichiometric proportion of chlorine to satisfy the following reactions:

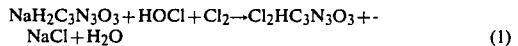
(1)

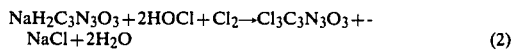
(2)

If it is desired to produce dichloroisocyanuric acid, the stoichiometric proportion of gaseous chlorine is illustrated in Equation (1) above. If it is desired to produce trichloroisocyanuric acid, the stoichiometric proportion of gaseous chlorine is illustrated above in Equation (2).

In order to enhance the reaction rate and completeness of the reaction, it is essential to add at least the stoichiometric proportion of gaseous chlorine required for the desired reaction. Generally from about 1 to about 2 times the stoichiometric proportion and preferably from about 1.1 to about 1.2 times the stoichiometric proportion of gaseous chlorine is added to the reactant for optimum reaction conditions.

The cross sectional area of each gas sparger may be the same or may be varied wherein the ratio of the cross sectional area of each of the feed lines may range from about 1:1 to about 3:1. For example, when there are two gas spargers for gaseous chlorine, one of the gas spargers may have an inside diameter of about 4 inches and the other gas sparger may have an inside diameter of about 2 inches when the reaction vessel has a capacity of 6,000 gallons. However, any suitable pipe sizes may be employed.

In addition, the proportion of chlorine fed through each gas sparger will depend to some extent on the cross sectional area of each gas sparger. The ratio of the proportion of chlorine fed from one gas sparger or feed location to the others may range from about 1:1 to about 4:1. One of the problems encountered in feeding gaseous chlorine through a single gas sparger of a glass lined reactor of this type is that the central agitator produces a vertical conical shaped vortex which markedly increases the liquid gaseous interface within the reactor. As a result, a significant proportion of the free chlorine dispersed below the liquid level escapes from the liquid medium into the gaseous phase before it has an opportunity to react with the components of the liquid medium. When a plurality of gas spargers is employed in accordance with this invention and each gas sparger is located in a different segment, not only is there a substantial reduction in the amount of excess chlorine required to achieve complete reaction, but also there is a substantial reduction in the amount of scaling of unreacted monosodium cyanurate on the interior of the reactor walls in the relatively quiescent zones. Placing a plurality of gas spargers through the horizontal cross sectional area of the reactor in accordance with this invention enhances the reaction rate and eliminates the quiescent areas where scaling occurs.

The following example is presented to define the invention more fully without any intention of being limited thereby. All parts are by weight unless otherwise specified.

EXAMPLE

A 6,000 gallon lined jacketed reactor having two finger baffles secured to the top of the reactor was employed. An aqueous solution of monosodium cyanurate and hypochlorous acid was fed continuously to the reactor. A central agitator was used to agitate the liquid medium while chlorine gas was provided through two spargers positioned approximately 180° apart behind each baffle. One sparger had a side diameter of 4" and the other had a diameter of 2". The chlorine gas was continuously fed to the reactor at a temperature of approximately 60° C. and a pressure of 15 psig. Each sparger was manufactured of Teflon coated steel which were about 135" long, having a wetted length of about 128" and a perforated tip of about 24" at the lower end of the sparger. Over a 9 month period, the ratio of chlorine consumed per unit of trichloroisocyanuric acid was established and was found to be approximately 0.524 pound of chlorine per pound of trichloroisocyanuric acid produced.

For purposes of comparison, the procedure was repeated using only a single 4" sparger to feed all of the chlorine to the reactor vessel. Over an 8 month period, the average chlorine consumption was 0.573 pound of chlorine per pound of trichloroisocyanuric acid produced. This difference corresponded to a consumption of 5,000 pounds of chlorine per day greater than was obtained when the double spargers of this invention were employed, using both a 4" diameter sparger as well as a 2" diameter sparger. In addition, when only a single sparger was employed, caking of the monosodium cyanurate on the side of the reaction vessel opposite from the sparger occurred due to the formation of a quiescent zone.

Thus it can be seen that there is a substantial reduction in chlorine consumption and diminishing of caking of the monosodium cyanurate when two spargers are used in accordance with the process of this invention.

What is claimed is:

1. A method for reacting gaseous halogen with a liquid medium comprised of an aqueous solution selected from the group consisting of an aqueous solution of a mixture of isocyanuric acid and sodium hydroxide and an aqueous solution of a mixture of sodium cyanurate and hypochlorous acid to form a halogenated isocyanuric acid reaction product in an agitated reaction zone having a perimeter and a horizontal cross sectional area divided into a plurality of segments which comprises contacting said gaseous halogen with said liquid medium in said reaction zone through a plurality of feed locations, each of said feed locations being positioned in a different segment and located substantially equidistant from said perimeter.

2. The method of claim 1 wherein said gas is chlorine.

3. The method of claim 2 wherein said liquid medium is an aqueous solution of sodium cyanurate and hypochlorous acid.

4. The method of claim 3 wherein said reaction product is a chlorinated isocyanuric acid.

5. The method of claim 4 wherein said reaction product is trichloroisocyanuric acid.

6. The method of claim 4 wherein said reaction product is dichloroisocyanuric acid.

7. The method of claim 5 wherein two of said feed locations are employed which are located in opposite segments.

8. The method of claim 7 wherein the ratio of said proportion of gas fed from one of said feed locations to the proportion fed from the other of said feed locations is in the range from about 1:1 to about 4:1.

* * * * *